(12) United States Patent
Borisy et al.

(10) Patent No.: US 6,693,125 B2
(45) Date of Patent: Feb. 17, 2004

(54) COMBINATIONS OF DRUGS (E.G., A BENZIMIDAZOLE AND PENTAMIDINE) FOR THE TREATMENT OF NEOPLASTIC DISORDERS

(75) Inventors: Alexis Borisy, Boston, MA (US); Curtis Keith, Boston, MA (US); Michael A. Foley, Chestnut Hill, MA (US); Brent R. Stockwell, Boston, MA (US)

(73) Assignee: CombinatoRx Incorporated, Boston, MA (US)

( * ) Notice: Subject to any disclaimer, the term of this patent is extended or adjusted under 35 U.S.C. 154(b) by 0 days.

(21) Appl. No.: 09/768,870

(22) Filed: Jan. 24, 2001

(65) Prior Publication Data

US 2002/0165261 A1 Nov. 7, 2002

(51) Int. Cl.$^7$ ............... A61K 31/415; A61K 31/155
(52) U.S. Cl. ............................. 514/388; 514/631
(58) Field of Search ........................... 514/388, 631

(56) References Cited

U.S. PATENT DOCUMENTS

| | | |
|---|---|---|
| 5,770,585 A | 6/1998 | Kaufman et al. |
| 6,280,768 B1 * | 8/2001 | McDevitt ............... 424/464 |

FOREIGN PATENT DOCUMENTS

| | | | |
|---|---|---|---|
| GB | 1288376 | 9/1972 | |
| WO | WO 01/35935 | 5/2001 | ............ 31/155 |

OTHER PUBLICATIONS

The Merck Index, eleventh edition, 1989, Merck & Co., Inc., Rayway, N. J., p. 1128, No. 7071.*
Anees et al., "Inhibition of a Tumor Protease with 3,4–Dichloroisocoumarin, Pentamidine–Isethionate and Guanidino Derivatives," *J. Enzyme Inhibition*, 8:213–221, 1994.
Bailly et al., "Sequence–Selective Binding to DNA of Bis(Amidinophenoxy)Alkanes Related to Propamidine and Pentamidine," *Biochem J.*, 323:23–31, 1997.
Barrett et al., "Anti–Sleeping Sickness Drugs and Cancer Chemotherapy," *Parasitology Today*, 16:7–9, 2000.
Bornstein et al., "An Evalution of the Mechanism of Action of Pentamidine Isethionate," *Journal of Surgical Oncology*, 2:393–398, 1970.
Cresson et al., " In Vitro Inhibition of Human Sarcoma Cells' Invasive Ability by Bis(5–Amidino–2–Benzimidazolyl) Methane–a novel esteroprotease inhibitor," *Am. J. Pathol.* 123:46–56, 1986.
Ferroni et al., "N1–Substituted Benzamidines: Synthesis, Antiproteinase Activity and Inhibition of Tumor Cell Growth," *II Farmaco*, 46:1311–1321, 1991.
Fibach et al., "Phorbol Ester–Induced Adhesion of Murine Erythroleukemia Cells: Possible Involvement of Cellular Proteases," *Carcinogenesis*, 4:1395–1399, 1983.
Fraser et al., "Endo–Exonuclease of Human Leukaemic Cells: Evidence for a Role in Apoptosis," *J. Cell Sci.*, 109:2343–2360, 1996.
Gambari et al., " DNA–Binding Activity and Biological effects of Aromatic Polyamidines," *Biochem Pharmacol*, 47:599–610, 1994.
Klemes et al., "Inhibition of Phorbol–Ester–Induced Adhesion of Differentiating Human Myeloid Leukemic Cells by Pentamidine–Isethionate," *Differentiation*, 27:141–145, 1984.
Kopac, M.J., "Section of Biology," *The New York Academy of Sciences*, 5–10, 1945.
Kopac, M.J., "Some Cellular and Surface Chemical Aspects of Tumor Chemotherapy," *Approaches to Tumor Chemotherapy* ed. F.R. Moulton, *AAAS*, Washington, D.C. 1947.
Libby et al., "Inhibition of Enzymes of Polyamine Back–Conversion by Pentamidine and Berenil," *Biochemical Pharmacology*, 44:830–832, 1992.
Luck et al., "Interaction of Nonintercalative Antitumour Drugs SN–6999 and SN–18071 with DNA: Influence of Ligand Structure on the Binding Specificity," *Journal of Biomolecular Structure & Dynamics* 4:1079–1094, 1987.
Nastruzzi et al., "Inhibition of 'In Vitro' Tumor Cell Growth by Aromatic Polyamidines Exhibiting Antiproteinase Activity," *Clin. Expl. Metastasis*, 7:25–39, 1989.
Nastruzzi et al., "Differential Effects of Benzamidine Derivatives on the Expression of C–MYC and HLA–DRα Genes in a Human B–Lymphoid Tumor Cell Line," *Cancer Letters*, 38:297–305, 1988.
Nishimura et al., "A Serine Protease–Inhibitory Benzamidine Derivative Inhibits the Growth of Human Colon Carcinoma Cells," *Jpn. J. Cancer Res.*, 83:723–728, 1992.
Osei et al., "Diabetogenic Effect of Pentamidine," *Am. J. Med.*, 77:41–46, 1984.
Perez et al., "Binding of Pt–Pentamidine to Nucleosomal DNA. Studies of the Antiproliferative Activity of the Drug Against Human Cancer Cells," *Chemico–Biological Interactions*, 89:61–72, 1993.
Perez et al., "DNA Binding Properties and Antileukemic (L1210) Activity of A Pt–Pentamidine Complex," *Chem. Biol. Interactions*, 77:341–355, 1991.
Reddy et al., "Synthetic DNA Minor Groove–Binding Drugs," *Pharmacology & Therapeutics*, 84:1–111, 1999.
Sands et al., "Pentamidine: A Review," *Reviews of Infectious Diseases*, 7:625–634, 1985.
Sansom et al., "Structural Studies on Bio–Active Compounds. Part XIV. Molecular Modelling of the Interactions Between Pentamidine and DNA," *Anti–Cancer Drug Design*, 5:243–248, 1990.

(List continued on next page.)

*Primary Examiner*—Jerome D. Goldberg
(74) *Attorney, Agent, or Firm*—Clark & Elbing LLP

(57) ABSTRACT

The invention features a method for treating a patient having a cancer or other neoplasm, by administering to the patient (i) a benzimidazole or a metabolite or analog thereof; and (ii) pentamidine or a metabolite or analog thereof simultaneously or within 14 days of each other in amounts sufficient to inhibit the growth of the neoplasm.

43 Claims, No Drawings

OTHER PUBLICATIONS

Schoenbach et al., "The Pharmacology, Mode of Action and Therapeutic Potentialities of Stilbamidine, Pentamidine, Propamidine and other Aromatic Diamidines–A Review," *Medicine*, 27:327–377, 1948.

Snapper, I., "Stilbamidine and Pentamidine in Multiple Myeloma," *J.A.M.A.*, 133:157–161., 1947.

Snapper, I., "On the Influence of Stilbamidine Upon Multiple Myeloma," *Journal of the Mount Sinai Hospital*, 8:119–127, 1946.

Turner et al., "The Mutagenic Properties of DNA Minor–Groove Binding Ligands," *Mutation Research*, 355:141–169, 1996.

Van Wauwe et al., "The Inhibitory Effect of Pentamidine on the Production of Chemotactic Cytokines by In Vitro Stimulated Human Blood Cells," *Inflamm. Res.* 45:357–363, 1996.

Waalkes et al., Pentamidine Clinical Pharmacologic Correlations in Man and Mice, *Clinical Pharmacology & Therapeutics*, 11:505–512, 1970.

National Cancer Institute Developmental Therapeutics Program In–Vitro Testing Results, NSC 620107 Experiment ID 9407SR53–57, 1994.

Al–Abdely et al., "Efficacies of KY62 Against *Leishmania amazonensis* and *Leishmania donovani* in Experimental Murine Cutaneous Leishmaniasis and Visceral Leishmaniasis" *Antimicrob. Agents Chemother*. 42:2542–2548 (1998).

Bailly et al., "Sequence–Specific DNA Minor Groove Binders. Design and Synthesis of Netropsin and Distamycin Analogues" *Bioconjug. Chem.*, 9:513–38 (1998).

Bailly et al., "Sequence–Selective Binding to DNA of bis(a–midinophenoxy) Alkanes Related to Propamidine and Pentamidine" *Biochem. J.* 323:23–31 (1997).

Bell et al., "Structure–Activity Relationships of Pentamidine Analogs Against *Giardia lamblia* and Correlation of Antigiardial Activity with DNA–Binding Affinity" *Antimicrob. Agents Chemother*. 35:1099–107 (1991).

Benaim et al., "A Calmodulin–Stimulated Ca2+ Pump in Plasma–Membrane Vesicles from *Trypanosoma brucei*; Selective Inhibition by Pentamidine" *Biochem. J*, 296:759–763 (1993).

Capece et al., "Pharmacokinetic Behaviour of Albendazole Sulphoxide Enantiomers in Male and Female Sheep" *Vet. Res. Commun.* 24:339–48 (2000).

Chen et al., "Anti–Tumor Necrosis Factor Properties of Non–Peptide Drugs in Acute–Phase Responses" *Eur. J. Pharmacol* 271:319–327 (1994).

Chiap et al., "Determination of Albendazole and Its Main Metabolites in Ovine Plasma by Liquid Chromatography with Dialysis as an Integrated Sample Preparation Technique" *J. Chromatogr. A*, 870:121–34 (2000).

Corsini et al., "Induction of Tumor Necrosis Factor–Alpha In Vivo by a Skin Irritant, Tributytin, Through Activation of Transcription Factors: Its Pharmacological Modulation by Anti–Inflammatory Drugs" *J. Invest. Dermatol.* 108:892–896 (1997).

Cubria et al., "Aromatic Diamidines are Reversible Inhibitors of Porcine Kidney Diamine Oxidase" *Biochem. Pharmacol.* 45:1355–7 (1993).

Dautzenberg et al., "Pentamidine Aerosol in the Preventive Treatment of Pheumocystosis in AIDS Patients. Comparison of Two Salts and Two Nebulizers" *Presse Med.* 20:1117–1120 (1991).

Del Posta et al., "Structure–In Vitro Activity Relationships of Pentamidine Analogues and Dication–Substituted Bis–Benzimidazoles as New Antifungal Agents" *Antimicrob. Agents Chemother*. 42:2495–2502 (1998).

Fimognari et al., "Flow Cytometric Analysis of Genetic Damage, Effect on Cell Cycle Progression, and Apoptosis by Thiophanate–Methyl in Human Lymphocytes" *Environ. Mol. Mutagen.* 33:173–176 (1999).

Ferroni et al., "N1–Substituted Benzamidines: Synthesis, Antiproteinase Activity and Inhibition of Tumor Cell Growth" *Farmaco* 46:1311–21 (1991).

Gupta, "Cross–Resistance of Nocodazole–Resistant Mutants of CHO Cells Toward Other Microtubule Inhibitors:Similar Mode of Action of Benzimidizole Carbamate Derivatives and NSC 181928 and TN–16" *Mol. Pharmacol.* 30:142–148 (1986).

Herberich et al., "Synthesis of a Netropsin Conjugate of a Water–Soluble epi–Quinocarin Analogue: the Importance of Stereochemistry at Nitrogen" *Bioorganic & Medicinal Chemistry* 8:523–532 (2000).

Hung et al., "Understanding and Controlling the Cell Cycle with Natural Products" *Chemistry & Biology*, 3:623–639 (1996).

Ingold et al., "Efficacies of Albendazole Sulfoxide and Albendazole Sulfone Against In Vitro–Cultivated *Echinococcus Multilocularis Metacestodes*" *Antimicrob. Agents Chemother*, 43:1052–61 (1999).

Kim et al., "Effects of Calmodulin Antagonists and Anesthetics on the Skin Lesions Induced by 2–Chloroethylethyl Sulfide" *Eur. J. Pharmacol*. 313:107–114 (1996).

Kitamura et al., "Inhibition of Constitutive Nitric Oxide Synthase in the Brain by Pentamidine, a Calmodulin Antagonists" *Eur. J. Pharmacol*. 289:299–304 (1995).

Marques et al., "Enantioselective Kinetic Disposition of Albendazole Sulfoxide in Patients with Neurocysticercosis" *Chirality* 11:218–223 (1999).

Mesa–Valle et al., "In Vitro Action of Platinum (II) and Platinum (IV) Complexes on *Trypanosoma cruzi* and *Leishmania donovani*" *Arzneimittelforschung* 39:838–42 (1989).

Mesa–Valle et al., "In Vitro and In Vivo Activity of Two Pt(IV) Salts Against *Leishmania donovanl*" *Pharmacology*, 57:160–172 (1998).

Mesa–Valle CM et al., "Action of New Organometallic Complexes Against *Leishmania donovani*" *J. Antimicrob. Chemother*. 40:47–57 (1997).

Monglardo et al., "Pentamidine Salts" *Lancet* 2:108 (1989).

Morgan et al, "Activities of Several Benzimidazoles and Tubulin Inhibitors Against Giardia spp. In Vitro" *Antimicrob. Agents Chemother*, 37:328–31 (1993).

Navas et al., "Structural Determinants of Putrescine Uptake Inhibition Produced by Cationic Diamidines in the Model of *Trypanosomatid Crithidla Fasciculata*" *Biol. Chem*, 377:833–6 (1996).

Nunn et al., "Sequence–Dependent Drug Binding to the Minor Groove of DNA; Crystal Structure of the DNA Dodecamar d(CGCAAATTTGCG)$_2$ Complexed with Propamidine" *J. Med. Chem.* 28:2317–2325 (1995).

Perez et al., "DNA Binding Properties and Antileukemic (L1210) Activity of Pt–Pentamidine Complex" *Chem. Biol. Interact*. 77:341–55 (1991).

Perez et al., "Binding of Pt–Pentamidine to Nucleosomal DNA. Studies of the Antiproliferative Activity of the Drug Against Human Cancer Cells" *Chemico–Biological Interactions* 89:61–72 (1993).

Ramanathan et al., "Determination of the Antifiarial Drug UMF–078 and its Metabolites UMF–080 and Flubendazole in Whole Blood Using High–Performance Liquid Chromatography" *J. Chromatogr. B Biomed. Appl*, 655:269–273 (1994).

Redondo et al., "Influence of Surfactants on Oral Bioavailability of Albendazole Based on the Formation of the Sulphoxide Metabolites in Rats" *Biopharm. Drug Dispos.*, 19:65–70 (1998).

Rolin et al., "Study of the In Vitro Bioactivation of Albendazole in Human Liver Microsomes and Hepatoma Cell Lines" *Cell Biol. Toxicol*. 5:1–14 (1998).

Rosenthal et al., "Pentamidine: An inhibitor of Interleukin–1 that Acts Via a Post–Translational Event" *Toxicol. App. Pharmacol*. 107:555–561 (1991).

Shapiro et al., "Selective Cleavage of Kinetoplast DNA Minicircles Promoted by Antitrypanosomal Drugs" *Proc. Natl. Acad. Sci. USA*, 87:950–954 (1990).

Tidwell et al., "Analogues of 1,5–Bis(4–amidlnophenoxy)pentane (Pentamidine) in the Treatment of Experimental *Pneumocystis carinii* Pneumonia" *J. Med. Chem*. 33:1252–1257 (1990).

Van Wauwe et al., "The Inhibitory Effect of Pentamidine on the Production of Chemotactic Cytokines by In Vitro Stimulated Human Blood Cells" *Inflamm. Res*. 45:357–363 (1996).

Whittaker et al., "Effects of Benzimidazole Analogs on Cultures of Differentiating Rodent Embryonic Cells" *Toxicol. Appl. Pharmacol*. 113:144–51 (1992).

Zakrzewska et al., "The Solvation Contribution to the Binding Energy of DNA with Non–Intercalating Antibiotics" *Nucleic Acids Res*. 12:6559–74 (1984).

Mesa–Valle et al., "In Vitro and In Vivo Activity of Two Pl(IV) Salts Against *Leishmania donovanl*" *Pharmacology*, 57:160–172 (1998).

* cited by examiner

COMBINATIONS OF DRUGS (E.G., A BENZIMIDAZOLE AND PENTAMIDINE) FOR THE TREATMENT OF NEOPLASTIC DISORDERS

BACKGROUND OF THE INVENTION

The invention relates to the treatment of neoplastic disorders such as cancer.

Cancer is a disease marked by the uncontrolled growth of abnormal cells. The abnormal cells may no longer do the work of normal cells, and they crowd out and destroy healthy tissue.

Lung cancer is the most common cancer-related cause of death among men and women. It is the second most commonly occurring cancer among men and women; it has been estimated that there will be more than 164,000 new cases of lung cancer in the U.S. in the year 2000 alone. While the rate of lung cancer cases is declining among men in the U.S., it continues to increase among women. Lung cancer can be lethal; according to the American Lung Association, an estimated 156,900 Americans are expected to die due to lung cancer in 2000.

Cancers that begin in the lungs are divided into two major types, non-small cell lung cancer and small cell lung cancer, depending on how the cells appear under a microscope. Non-small cell lung cancer (squamous cell carcinoma, adenocarcinoma, and large cell carcinoma) generally spreads to other organs more slowly than does small cell lung cancer. Small cell lung cancer is the less common type, accounting for about 20% of all lung cancer.

Other cancers include brain cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, and uterine cancer. These cancers, like lung cancer, are sometimes treated with chemotherapy.

Chemotherapeutic drugs currently in use or in clinical trials include paclitaxel, docetaxel, tamoxifen, vinorelbine, gemcitabine, cisplatin, etoposide, topotecan, irinotecan, anastrozole, rituximab, trastuzumab, fludarabine, cyclophosphamide, gentuzumab, carboplatin, interferon, and doxorubicin. The most commonly used anticancer agent is paclitaxel, which is used alone or in combination with other chemotherapy drugs such as: 5-FU, doxorubicin, vinorelbine, cytoxan, and cisplatin.

SUMMARY OF THE INVENTION

We have discovered that the combination of one of the antihelmintic drugs albendazole, mebendazole, or oxibendazole and the antiprotozoal drug pentamidine exhibits substantial antiproliferative activity against cancer cells. Structural and functional analogs of each of these compounds are known, and any of these analogs can be used in the antiproliferative combinations of the invention. Metabolites of albendazole and pentamidine are also known. Many of these metabolites share one or more biological activities with the parent compound and, accordingly, can also be used in the antiproliferative combinations of the invention. Accordingly, the invention features a method for treating a patient having a cancer or other neoplasm, by administering to the patient (i) albendazole, mebendazole, or oxibendazole; and (ii) pentamidine simultaneously or within 14 days of each other in amounts sufficient to inhibit the growth of the neoplasm.

Preferably, the two compounds are administered within ten days of each other, more preferably within five days of each other, and most preferably within twenty-four hours of each other or even simultaneously. The cancer treated according to any of the methods of the invention, described below, can be lung cancer (squamous cell carcinoma, adenocarcinoma, or large cell carcinoma), brain cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, or uterine cancer.

In a related aspect, the invention also features a method for treating a patient having a neoplasm such as cancer. In this method, the patient is administered (a) a first compound selected from albendazole, albendazole sulfonate, albendazole sulfone, albendazole sulfoxide, astemizole, benomyl, 2-benzimidazolylurea, benzthiazuron, cambendazole, cyclobendazole, domperidone, droperidol, fenbendazole, flubendazole, frentizole, 5-hydroxymebendazole, lobendazole, luxabendazole, mebendazole, methabenzthiazuron, mercazole, midefradil, nocodozole, omeprazole, oxfendazole, oxibendazole, parbendazole, pimozide, and tioxidazole (or a salt of any of the above), NSC181928 (ethyl 5-amino-1,2-dihydro-3-[(N-methylanilino)methyl]-pyrido[3,4-b]pyrazin-7-ylcarbamate), and TN-16 (3-(1-anilinoethylidene)-5-benzyl-pyrrodiline-2,4-dione); and (b) a second compound selected from pentamidine, propamidine, butamidine, heptamidine, nonamidine, stilbamidine, hydroxystilbamidine, diminazene, benzamidine, phenamidine, dibrompropamidine, 1,3-bis(4-amidino-2-methoxyphenoxy)propane, phenamidine, and amicarbalide (or a salt of any of the above). Alternatively, the second compound can be a functional analog of pentamidine, such as netropsin, distamycin, bleomycin, actinomycin, or daunorubicin. The first and second compounds are preferably administered simultaneously or within 14 days of each other and in amounts sufficient to inhibit the growth of the neoplasm.

In another related aspect, the invention also features a method for treating a patient having a neoplasm such as cancer by administering the following:

a) a first compound having the formula (I):

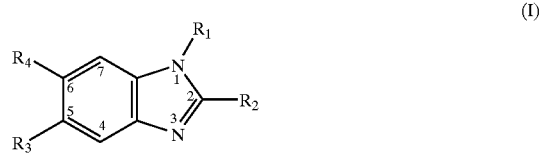

(I)

wherein:

$R_1$ is selected from the group consisting of:

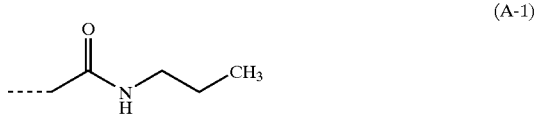

(A-1)

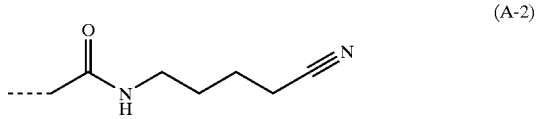

(A-2)

-continued
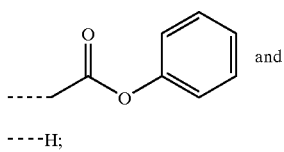
(A-3)
----H; (A-4)
$R_2$ is selected from the group consisting of:
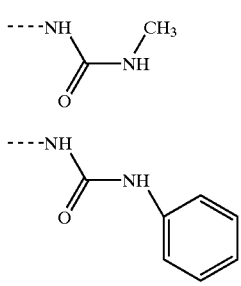
(B-1)
(B-2)
----NH$_2$ (B-3)
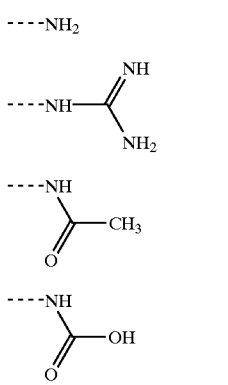
(B-4)
(B-5)
(B-6)
(B-7)
(B-8)
(B-9)
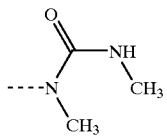
(B-10)
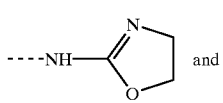
(B-11)
(B-12)
-continued
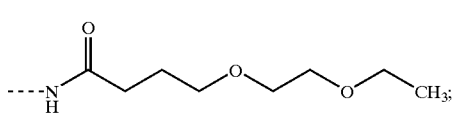
(B-13)
each of $R_3$ and $R_4$ is independently selected from the group consisting of:
----Cl (C-1)
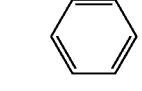
(C-2)
(C-3)
(C-4)
----OCH$_3$ (C-5)
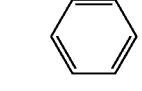
(C-6)
(C-7)
(C-8)
(C-9)
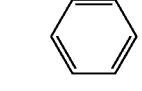
(C-10)
----CH$_3$ (C-11)
(C-12)

-continued (C-13) 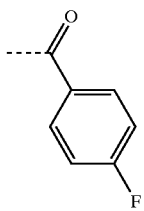

(C-14) 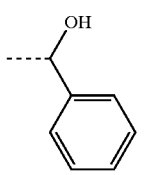

(C-15) 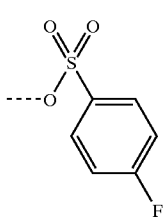

(C-16) 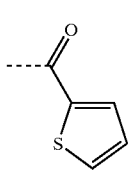

(C-17) 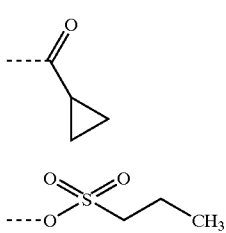

(C-18) 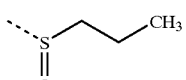

(C-19) 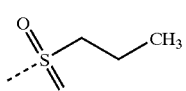

(C-20) 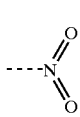

(C-21) ----H (C-22) ----CH$_3$ (C-23) 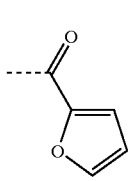

(C-24) 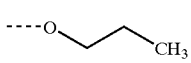

-continued (C-25) -----F and (C-26) ----Br;

(C-27)

and b) a second compound having the formula (II):

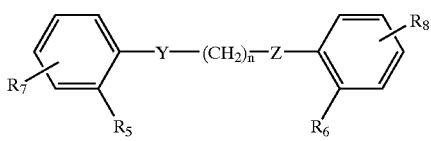

(II)

wherein each of Y and Z is, independently, O or N; each of $R_5$ and $R_6$ is, independently, —H, —OH, -halogen, —O—$C_{1-10}$ alkyl, —OCF$_3$, —NO$_2$, or NH$_2$; n is an integer between 2 and 6, inclusive; and each of $R_7$ and $R_8$ is, independently, at the meta or para position and is selected from the group consisting of:

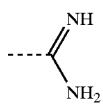 (D-1)

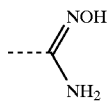 (D-2)

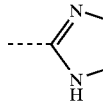 (D-3)

(D-4) 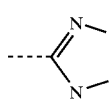 and (D-5) 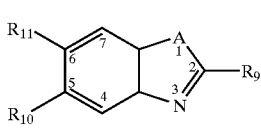

wherein the first and second compounds are administered simultaneously or within 14 days of each other in amounts sufficient to inhibit the growth of the neoplasm.

In another related aspect, the invention also features a method for treating a patient having a neoplasm such as cancer by administering the following:

a) a first compound having the formula (III):

(III)

wherein:

A is selected from the group consisting of O, S, and NR$_{12}$;

$R_9$ is selected from the group consisting of:

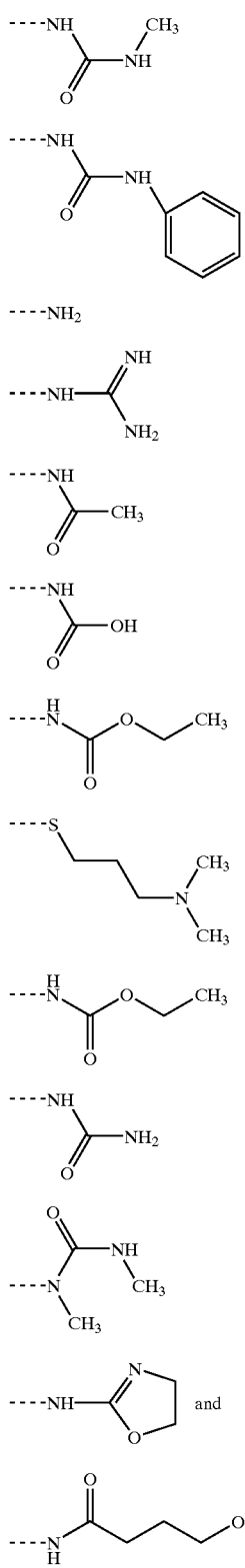

each of $R_{10}$ and $R_{11}$ is independently selected from the group consisting of —H, -halo, —$NO_2$, —OH, —SH, —O—$C_{1-10}$ alkyl, —O—($C_{1-10}$)$_{0-1}$-aryl, —O—($C_{1-10}$ alkyl)$_{0-1}$-heteroaryl, —O—($C_{1-10}$ alkyl)$_{0-1}$-heterocyclyl, —$C_{1-10}$ alkoxycarbonyl, —$S(O)_{0-2}$—$C_{1-10}$ alkyl, —$S(O)_{0-2}$—($C_{1-10}$ alkyl)$_{0-1}$-aryl, —$S(O)_{0-2}$—($C_{1-10}$ alkyl)$_{0-1}$-heteroaryl, —$S(O)_{0-2}$—$C_{1-10}$ alkyl)$_{0-1}$-heterocyclyl, and —$C_{1-10}$ alkyl or —$C_{2-10}$ alkenyl that is unsubstituted or substituted by one or more substituents selected from the group consisting of -aryl, -heteroaryl, -heterocyclyl, —O—$C_{1-10}$ alkyl, —O—($C_{1-10}$ alkyl)$_{0-1}$-aryl, —O—($C_{1-10}$ alkyl)$_{0-1}$-heteroaryl, —O—($C_{1-10}$ alkyl)$_{0-1}$-heterocyclyl, —$C_{1-10}$ alkoxycarbonyl, —$S(O)_{0-2}$—$C_{1-10}$ alkyl, —$S(O)_{0-2}$—($C_{1-10}$ alkyl)$_{0-1}$-aryl, —$S(O)_{0-2}$—($C_{1-10}$ alkyl)$_{0-1}$-heteroaryl, —$S(O)_{0-2}$—($C_{1-10}$ alkyl)$_{0-1}$-heterocyclyl, —$N(R_{13})_2$, —$OR_{13}$, -oxo, -cyano, -halogen, —$NO_2$, —OH, and —SH;

$R_{12}$ is selected from the group consisting of —H and —$C_{1-10}$ alkyl or —$C_{2-10}$ alkenyl that is unsubstituted or substituted by one or more substituents selected from the group consisting of -aryl, -heteroaryl, -heterocyclyl, —O—$C_{1-10}$ alkyl, —O—($C_{1-10}$)$_{0-1}$-aryl, —O—($C_{1-10}$ alkyl)$_{0-1}$-heteroaryl, —O—($C_{1-10}$ alkyl)$_{0-1}$-heterocyclyl, —$C_{1-10}$ alkoxycarbonyl, —$S(O)_{0-2}$—$C_{1-10}$ alkyl, —$S(O)_{0-2}$-($C_{1-10}$ alkyl)$_{0-1}$-aryl, —$S(O)_{0-2}$—($C_{1-10}$ alkyl)$_{0-1}$-heteroaryl, —$S(O)_{0-2}$—($C_{1-10}$ alkyl)$_{0-1}$-heterocyclyl, —$N(R_{13})_2$, —$OR_{13}$, -oxo, -cyano, -halo, —$NO_2$, —OH, and —SH; and each $R_{13}$ is independently selected from the group consisting of H and $C_{1-10}$ alkyl or $C_{2-10}$ alkenyl that is unsubstituted or substituted by one or more substituents selected from the group consisting of -aryl, -heteroaryl, -heterocyclyl, —O—$C_{1-10}$ alkyl, —O—($C_{1-10}$)$_{0-1}$-aryl, —O—($C_{1-10}$ alkyl)$_{0-1}$-heteroaryl, —O—($C_{1-10}$ alkyl)$_{0-1}$-heterocyclyl, —$C_{1-10}$ alkoxycarbonyl, -oxo, -cyano, -halo, —$NO_2$, —OH, and —SH; and b) a second compound having the formula (II):

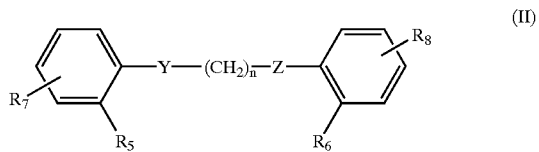

wherein each of Y and Z is, independently, O or N; each of $R_5$ and $R_6$ is, independently, —H, —OH, -halogen, —O—$C_{1-10}$ alkyl, —$OCF_3$, —$NO_2$, or $NH_2$; n is an integer between 2 and 6, inclusive; and each of $R_7$ and $R_8$ is, independently, at the meta or para position and is selected from the group consisting of:

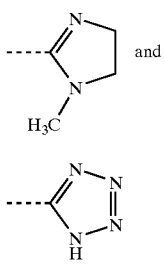

wherein the first and second compounds are administered simultaneously or within 14 days of each other in amounts sufficient to inhibit the growth of the neoplasm.

In any of the foregoing treatment methods, both compounds are preferably together in a pharmaceutical composition that also includes a pharmaceutically acceptable carrier. A benzimidazole is preferably administered at a dosage of 1 to 2500 milligrams and pentamidine is preferably administered at a dosage of 1 to 1000 milligrams. Suitable modes of administration include intravenous, intramuscular, inhalation, and oral administration.

The antiproliferative combinations of the invention can also be provided as components of a pharmaceutical pack. The two drugs can be formulated together or separately and in individual dosage amounts.

It will be understood by those in the art that the compounds are also useful when formulated as salts. For example, as is described herein, the isethionate salt of pentamidine exhibits synergistic antiproliferative activity when combined with a benzimidazole. Other salts of pentamidine include the platinum salt, the dihydrochloride salt, and the dimethanesulfonate salt (see, for example, Mongiardo et al., Lancet 2:108, 1989). Similarly, benzimidazole salts include, for example, halide, sulfate, nitrate, phosphate, phosphinate salts.

The invention also features a method for identifying compounds useful for treating a patient having a neoplasm. The method includes the steps of: contacting cancer cells in vitro with (i) pentamidine or a benzimidazole (or an analog of pentamidine or a benzimidazole) and (ii) a candidate compound, and determining whether the cancer cells grow more slowly than (a) cancer cells contacted with the benzimidazole or pentamidine but not contacted with the candidate compound, and (b) cancer cells contacted with the candidate compound but not with the benzimidazole or pentamidine. A candidate compound that, when combined with the benzimidazole or pentamidine, reduces cell proliferation but, in the absence of the benzimidazole or pentamidine, does not is a compound that is useful for treating a patient having a neoplasm.

Combination therapy according to the invention may be provided wherever chemotherapy is performed: at home, the doctor's office, a clinic, a hospital's outpatient department, or a hospital. Treatment generally begins at a hospital so that the doctor can observe the therapy's effects closely and make any adjustments that are needed. The duration of the combination therapy depends on the kind of cancer being treated, the age and condition of the patient, the stage and type of the patient's disease, and how the patient's body responds to the treatment. Drug administration may be performed at any of various intervals (e.g., daily, weekly, or monthly) and the dosage, frequency, and mode of administration of each agent can be determined individually. Combination therapy may be given in on-and-off cycles that include rest periods so that the patient's body has a chance to build healthy new cells and regain strength.

Depending on the type of cancer and its stage of development, the combination therapy can be used to treat cancer, to slow the spreading of the cancer, to slow the cancer's growth, to kill or arrest cancer cells that may have spread to other parts of the body from the original tumor, to relieve symptoms caused by the cancer, or to prevent cancer in the first place. Combination therapy can also help people live more comfortably by eliminating cancer cells that cause pain or discomfort.

As used herein, the terms "alkyl," "alkenyl," and the prefix "alk-" are inclusive of both straight chain and branched chain groups and of cyclic groups, i.e., cycloalkyl and cycloalkenyl groups. Cyclic groups can be monocyclic or polycyclic and preferably have from 3 to 10 ring carbon atoms, inclusive. Exemplary cyclic groups include cyclopropyl, cyclopentyl, cyclohexyl, and adamantyl groups.

The term "aryl" includes carbocyclic aromatic rings or ring systems. Examples of aryl groups include phenyl, naphthyl, biphenyl, fluorenyl, and indenyl groups. The term "heteroaryl" includes aromatic rings or ring systems that contain at least one ring hetero atom (e.g., O, S, N). Heteroaryl groups include furyl, thienyl, pyridyl, quinolinyl, tetrazolyl, and imidazo groups.

"Hetercyclyl" includes non-aromatic rings or ring systems that contain at least one ring hetero atom (e.g., O, S, N). Heterocyclic groups include, for example, pyrrolidinyl, tetrahydrofuranyl, morpholinyl, thiazolidinyl, and imidazolidinyl groups.

The aryl, heteroaryl, and heterocyclyl groups may be unsubstituted or substituted by one or more substituents selected from the group consisting of $C_{1-10}$ alkyl, hydroxy, halo, nitro, $C_{1-10}$ alkoxy, $C_{1-10}$ alkylthio, trihalomethyl, $C_{1-10}$ acyl, arylcarbonyl, heteroarylcarbonyl, nitrile, $C_{1-10}$ alkoxycarbonyl, oxo, arylalkyl (wherein the alkyl group has from 1 to 10 carbon atoms) and heteroarylalkyl (wherein the alkyl group has from 1 to 10 carbon atoms).

Compounds useful in the invention include those described herein in any of their pharmaceutically acceptable forms, including isomers such as diastereomers and enantiomers, salts, solvates, and polymorphs, thereof, as well as racemic mixtures of the compounds described herein.

Other features and advantages of the invention will be apparent from the following detailed description, and from the claims.

DETAILED DESCRIPTION OF THE INVENTION

We have discovered that the antihelmentic drugs albendazole, mebendazole, or oxibendazole in combination with the antiprotozoal drug pentamidine exhibit substantial antiproliferative activity against cancer cells. Concentrations that exhibited maximal antiproliferative activity against cancer cells were not toxic to normal cells. Thus, this drug combination is useful for the treatment of cancer and other neoplasms. We have also discovered that the combination of pentamidine isethionate with either exhibits similar antiproliferative activity.

Based on known properties that are shared among albendazole, mebendazole, and oxibendazole, their metabolites, and other benzimidazoles, as well as those shared among pentamidine and its analogs and metabolites, it is likely that structurally related compounds can be substituted for albendazole, mebendazole, and oxibendazole and for pentamidine in the antiproliferative combinations of the invention. Information regarding each of the drugs and its analogs and metabolites is provided below.

Benzimidazoles

Benzimidazoles that are useful in the antiproliferative combination of the invention are compounds having the general formula (I):

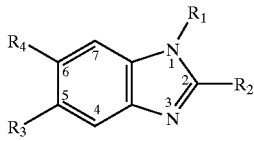
(I)

wherein:

$R_1$ is selected from the group consisting of H and $C_{1-10}$ alkyl or $C_{2-10}$ alkenyl that is unsubstituted or substituted by one or more substituents selected from the group consisting of -aryl, -heteroaryl, -heterocyclyl, $-O-C_{1-10}$ alkyl, $-O-(C_{1-10})_{0-1}$-aryl, $-O-(C_{1-10}$ alkyl$)_{0-1}$-heteroaryl, $-O-(C_{1-10}$ alkyl$)_{0-1}$-heterocyclyl, $-C_{1-10}$ alkoxycarbonyl, $-S(O)_{0-2}-C_{1-10}$ alkyl, $-S(O)_{0-2}-(C_{1-10}$ alkyl)0-1-aryl, $-S(O)_{0-2}-(C_{1-10}$ alkyl$)_{0-1}$-heteroaryl, $-S(O)_{0-2}-(C_{1-10}$ alkyl$)_{0-1}$-heterocyclyl, $-N(R_{13})_2$, $-OR_{13}$, -oxo, -cyano, -halo, $-NO_2$, $-OH$, and $-SH$;

$R_2$ is selected from the group consisting of:

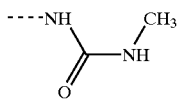
(B-1)

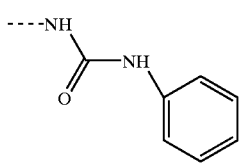
(B-2)

(B-3)
----NH$_2$

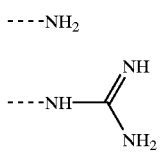
(B-4)

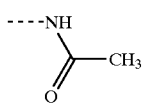
(B-5)

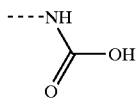
(B-6)

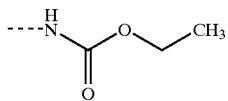
(B-7)

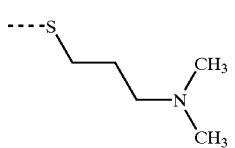
(B-8)

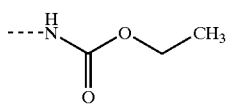
(B-9)

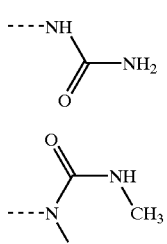
(B-10)

(B-11)

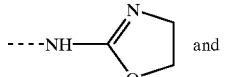
(B-12)

and

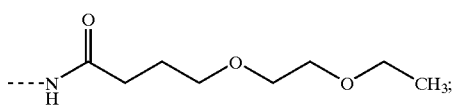
(B-13)

each of $R_3$ and $R_4$ is independently selected from the group consisting of $-H$, -halo, $-NO_2$, $-OH$, $-SH$, $-O-C_{1-10}$ alkyl, $-O-(C_{1-10})_{0-1}$-aryl, $-O-(C_{1-10}$ alkyl$)_{0-1}$—heteroaryl, $-O-(C_{1-10}$ alkyl$)_{0-1}$-heterocyclyl, $-C_{1-10}$ alkoxycarbonyl, $-S(O)_{0-2}-C_{1-10}$ alkyl, $-S(O)_{0-2}-(C_{1-10}$ alkyl$)_{0-1}$-aryl, $-S(O)_{0-2}-(C_{1-10}$ alkyl$)_{0-1}$-heteroaryl, $-S(O)_{0-2}-(C_{1-10}$ alkyl$)_{0-1}$-heterocyclyl, and $-C_{1-10}$ alkyl or $-C_{2-10}$ alkenyl that is unsubstituted or substituted by one or more substituents selected from the group consisting of -aryl, -heteroaryl, -heterocyclyl, $-O-C_{1-10}$ alkyl, $-O-(C_{1-10}$ alkyl$)_{0-1}$-aryl, $-O-(C_{1-10}$ alkyl$)_{0-1}$-heteroaryl, $-O-(C_{1-10}$ alkyl$)_{0-1}$-heterocyclyl, $-C_{1-10}$ alkoxycarbonyl, $-S(O)_{0-2}-C_{1-10}$ alkyl, $-S(O)_{0-2}-(C_{1-10}$ alkyl$)_{0-1}$-aryl, $-S(O)_{0-2}-(C_{1-10}$ alkyl$)_{0-1}$-heteroaryl, $-S(O)_{0-2}-(C_{1-10}$ alkyl$)_{0-1}$-heterocyclyl, $-N(R_{13})_2$, $-OR_{13}$, -oxo, -cyano, -halogen, $-NO_2$, $-OH$, and $-SH$; and each $R_{13}$ is selected from the group consisting of H and $C_{1-10}$ alkyl or $C_{2-10}$ alkenyl that is unsubstituted or substituted by one or more substituents selected from the group consisting of -aryl, -heteroaryl, -heterocyclyl, $-O-C_{1-10}$ alkyl, $-O-(C_{1-10})_{0-1}$-aryl, $-O-(C_{1-10}$ alkyl$)_{0-1}$-heteroaryl, $-O-(C_{1-10}$ alkyl$)_{0-1}$-heterocyclyl, $-C_{1-10}$ alkoxycarbonyl, -oxo, -cyano, -halo, $-NO_2$, $-OH$, and $-SH$.

Examples of substituents $R_1$, $R_3$, and $R_4$ are provided below.
$R_1$
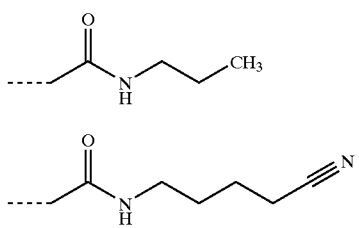 (A-1)
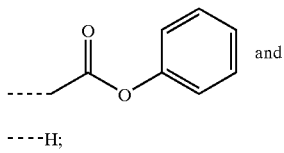 (A-2)
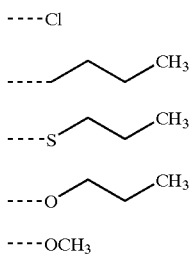 and (A-3)
----H; (A-4)
$R_3$ and $R_4$
----Cl (C-1)
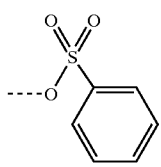 (C-2)
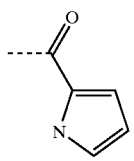 (C-3)
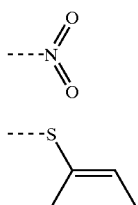 (C-4)
----OCH$_3$ (C-5)
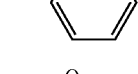 (C-6)
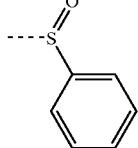 (C-7)
 (C-8)
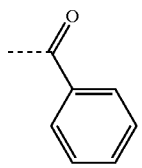 (C-9)
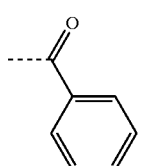 (C-10)
----CH$_3$ (C-11)
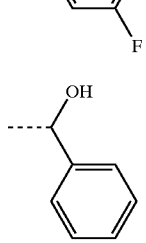 (C-12)
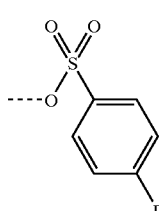 (C-13)
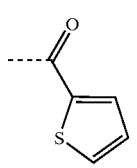 (C-14)
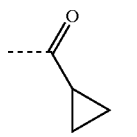 (C-15)
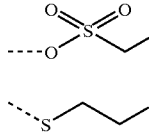 (C-16)
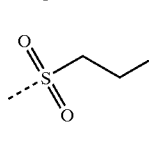 (C-17)
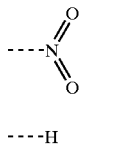 (C-18)
 (C-19)
(C-20)
(C-21)
----H (C-22)
----CH$_3$ (C-23)

-continued

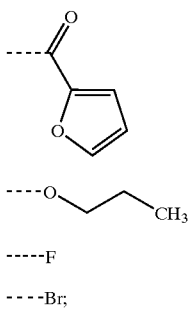
(C-24)

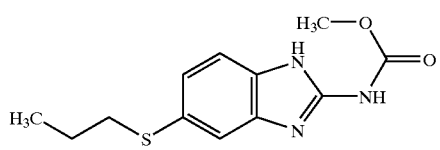
(C-25)

----F  (C-26)

----Br;  (C-27)

One of the most commonly prescribed members of the benzimidazole family is albendazole, which has the structure:

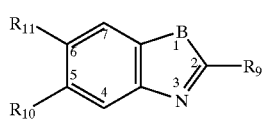
(E-1)

Albendazole is currently available as an oral suspension and in tablets.

Albendazole Metabolites

Albendazole undergoes metabolic transformation into a number of metabolites that may be therapeutically active; these metabolites may be substituted for albendazole in the antiproliferative combination of the invention. The metabolism of albendazole can yield, for example, albendazole sulfonate, albendazole sulfone, and albendazole sulfoxide.

Benzimidazole Analogs

Analogs of benzimidazoles include benzothioles and benzoxazoles having the structure of formula IV:

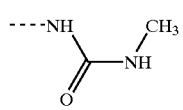
(IV)

wherein:

B is O or S;

$R_9$ is selected from the group consisting of:

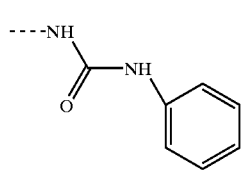
(B-1)

(B-2)

----NH$_2$  (B-3)

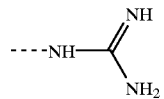
(B-4)

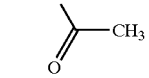
(B-5)

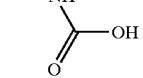
(B-6)

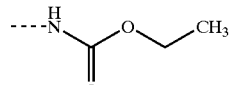
(B-7)

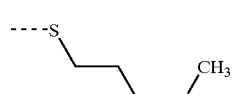
(B-8)

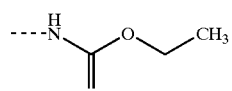
(B-9)

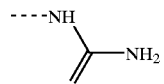
(B-10)

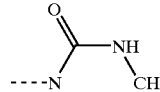
(B-11)

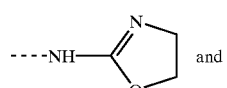
(B-12) and

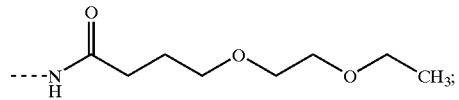
(B-13)

and each of $R_{10}$ and $R_{11}$ is independently selected from the group consisting of —H, -halo, —NO$_2$, —OH, —SH, —O—C$_{1-10}$ alkyl, —O—(C$_{1-10}$)$_{0-1}$-aryl, —O—(C$_{1-10}$ alkyl)$_{0-1}$-heteroaryl, —O—(C$_{1-10}$ alkyl)$_{0-1}$-heterocyclyl, —C$_{1-10}$ alkoxycarbonyl, —S(O)$_{0-2}$—C$_{1-10}$ alkyl, —S(O)$_{0-2}$-(C$_{1-10}$ alkyl)$_{0-1}$-aryl, —S(O)$_{0-2}$-(C$_{1-10}$ alkyl)$_{0-1}$-heteroaryl, —S(O)$_{0-2}$—(C$_{1-10}$ alkyl)$_{0-1}$-heterocyclyl, and —C$_{1-10}$ alkyl or —C$_{2-10}$ alkenyl that is unsubstituted or substituted by one or more substituents selected from the group consisting of -aryl, -heteroaryl, -heterocyclyl, —O-C$_{1-10}$ alkyl, —O—(C$_{1-10}$ alkyl)$_{0-1}$-aryl, —O—(C$_{1-10}$ alkyl)$_{0-1}$-heteroaryl, —O—(C$_{1-10}$ alkyl)$_{0-1}$-heterocyclyl, -C$_{1-10}$ alkoxycarbonyl, —S(O)$_{0-2}$—C$_{1-10}$ alkyl, —S(O)$_{0-2}$—(C$_{1-10}$ alkyl)$_{0-1}$-aryl, —S(O)$_{0-2}$—(C$_{1-10}$ alkyl)$_{0-1}$-heteroaryl, —S(O)$_{0-2}$—(C$_{1-10}$ alkyl)$_{0-1}$-heterocyclyl, —N(R$_{13}$)$_2$, —OR$_{13}$, -oxo, -cyano, -halogen, —NO$_2$, —OH, and —SH; and each $R_{13}$ is independently selected from the group consisting of H and $C_{1-10}$ alkyl or $C_{2-10}$ alkenyl that is unsubstituted or substituted by one or more substituents selected from the group consisting of -aryl, -heteroaryl, -heterocyclyl, —O—$C_{1-10}$ alkyl, —O—$(C_{1-10})_{0-1}$-aryl, —O—$(C_{1-10}$ alkyl$)_{0-1}$-heteroaryl, —O—$(C_{1-10}$ alkyl$)_{0-1}$-heterocyclyl, —$C_{1-10}$ alkoxycarbonyl, -oxo, -cyano, -halo, —$NO_2$, —OH, and —SH.

Suitable benzimidazoles and benzimidazole analogs for use in the methods of the invention include astemizole, benomyl, 2-benzimidazolylurea, benzthiazuron, cambendazole, cyclobendazole, domperidone, droperidol, fenbendazole, flubendazole, frentizole, 5-hydroxymebendazole, lobendazole, luxabendazole, mebendazole, methabenzthiazuron, mercazole, midefradil, nocodozole, omeprazole, oxfendazole, oxibendazole, parbendazole, pimozide, and tioxidazole.

Some benzimidazoles and benzimidazole analogs fit the following formula (III).

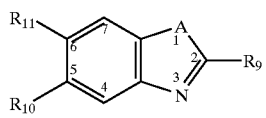

(III)

wherein:

A is selected from the group consisting of O, S, and $NR_{12}$;

$R_9$, $R_{10}$, $R_{11}$, and $R_{13}$ are as described above for formula (IV);

$R_{12}$ is selected from the group consisting of —H and —$C_{1-10}$ alkyl or —$C_{2-10}$ alkenyl that is unsubstituted or substituted by one or more substituents selected from the group consisting of -aryl, -heteroaryl, -heterocyclyl, —O—$C_{1-10}$ alkyl, —O—$(C_{1-10})_{0-1}$-aryl, —O—$(C_{1-10}$ alkyl$)_{0-1}$-heteroaryl, —O—$(C_{1-10}$ alkyl$)_{0-1}$-heterocyclyl, —$C_{1-10}$ alkoxycarbonyl, —$S(O)_{0-2}$—$C_{1-10}$ alkyl, —$S(O)_{0-2}$—$(C_{1-10}$ alkyl$)_{0-1}$-aryl, —$S(O)_{0-2}$—$(C_{1-10}$ alkyl$)_{0-1}$-heteroaryl, —$S(O)_{0-2}$—$(C_{1-10}$ alkyl$)_{0-1}$-heterocyclyl, —$N(R_{13})_2$, —$OR_{13}$, -oxo, -cyano, -halo, —$NO_2$, —OH, and —SH; and Pentamidine Pentamidine is currently used for the treatment of *Pneumocystis carinii, Leishmania donovani, Trypanosoma brucei, T. gambiense,* and *T. rhodesiense* infections. The structure of pentamidine is:

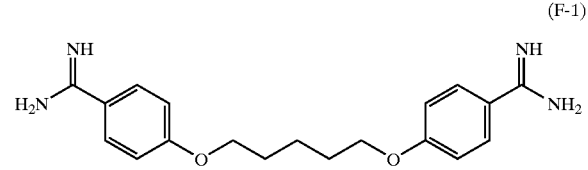

(F-1)

It is available formulated for injection or inhalation. For injection, pentamidine is packaged as a nonpyrogenic, lyophilized product. After reconstitution, it is administered by intramuscular or intravenous injection.

Pentamidine isethionate is a white, crystalline powder soluble in water and glycerin and insoluble in ether, acetone, and chloroform. It is chemically designated 4,4'-diamidino-diphenoxypentane di(β-hydroxyethanesulfonate). The molecular formula is $C_{23}H_{36}N_4O_{10}S_2$ and the molecular weight is 592.68.

The antiprotozoal mode of action of pentamidine is not fully understood. In vitro studies with mammalian tissues and the protozoan *Crithidia oncopelti* indicate that the drug interferes with nuclear metabolism, causing inhibition of the synthesis of DNA, RNA, phospholipids, and proteins.

Little is also known about the drug's pharmacokinetics. In one published study, seven patients treated with daily i.m. doses of pentamidine at 4 mg/kg for 10 to 12 days were found to have plasma concentrations between 0.3 and 0.5 µg/mL. The patients continued to excrete decreasing amounts of pentamidine in urine up to six to eight weeks after cessation of treatment.

Tissue distribution of pentamidine has been studied in mice given a single intraperitoneal injection of pentamidine at 10 mg/kg. The concentration in the kidneys was the highest, followed by that in the liver. In mice, pentamidine was excreted unchanged, primarily via the kidneys with some elimination in the feces. The ratio of amounts excreted in the urine and feces (4:1) was constant over the period of study.

Pentamidine Analogs

Aromatic diamidino compounds can replace pentamidine in the antiproliferative combination of the invention. These compounds are referred to as pentamidine analogs. Examples are propamidine, butamidine, heptamidine, and nonamidine, all of which, like pentamidine, exhibit antipathogenic or DNA binding properties. Other analogs (e.g., stilbamidine and indole analogs of stilbamidine, hydroxystilbamidine, diminazene, benzamidine, dibrompropamidine, 1,3-bis(4-amidino-2-methoxyphenoxy) propane (DAMP), netropsin, distamycin, phenamidine, amicarbalide, bleomycin, actinomycin, and daunorubicin) also exhibit properties in common with pentamidine. It is likely that these compounds will have antiproliferative activity when administered in combination with a benzimidazole (or an analog or metabolite of a benzimidazole).

Suitable analogs are those falling within formula (II).

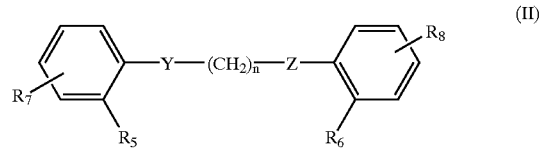

(II)

wherein each of Y and Z is, independently, —O— or —N—; each of $R_5$ and $R_6$ is, independently, —H, —OH, —Cl, —Br, —F, —$OCH_3$, —$OCF_3$, —$NO_2$, or —$NH_2$; n is an integer between 2 and 6, inclusive; and each of $R_7$ and $R_8$ is, independently, at the meta or para position and is selected from the group consisting of:

(D-1)

(D-2)

(D-3)

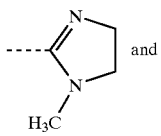 (D-)

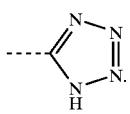 (D-5)

Other suitable pentamidine analogs include stilbamidine (G-1) and hydroxystilbamidine (G-2), and their indole analogs (e.g., G-3):

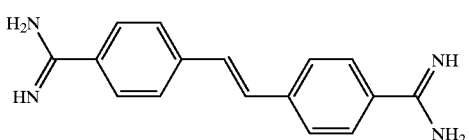 (G-1)

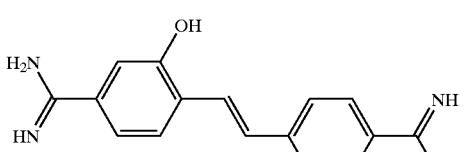 (G-2)

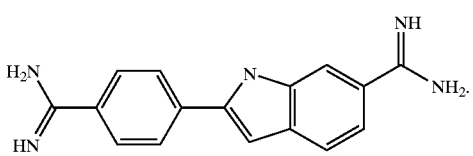 (G-3)

Each amidine moiety may independently be replaced with one of the moieties depicted as D-2, D-3, D-4, or D-5, above. As is the case for the benzimidazoles and pentamidine, salts of stilbamidine, hydroxystilbamidine, and their indole derivatives are also useful in the method of the invention. Preferred salts include, for example, dihydrochloride and methanesulfonate salts.

Pentamidine Metabolites

Pentamidine metabolites are also useful in the antiproliferative combination of the invention. Pentamidine is rapidly metabolized in the body to at least seven primary metabolites. Some of these metabolites share one or more activities with pentamidine. It is likely that some pentamidine metabolites will exhibit antiproliferative activity when combined with a benzimidazole or an analog thereof.

Seven pentamidine metabolites are shown below.

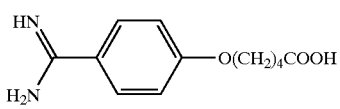 (H-1)

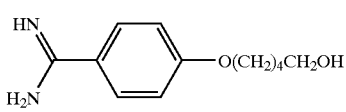 (H-2)

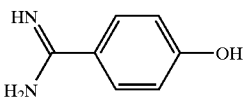 (H-3)

 (H-4)

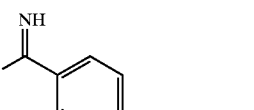 (H-5)

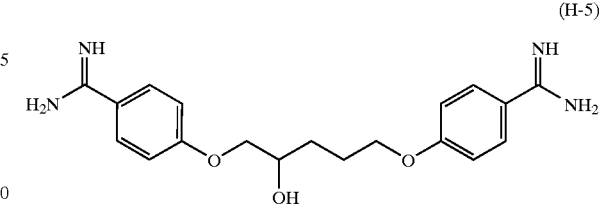 (H-5)

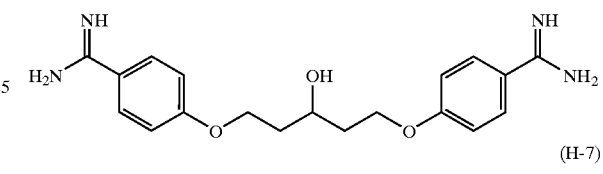 (H-6)

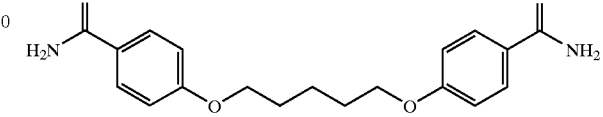 (H-7)

Therapy

The combinations of compounds of the invention are useful for the treatment of neoplasms. Combination therapy may be performed alone or in conjunction with another therapy (e.g., surgery, radiation, chemotherapy, biologic therapy). Additionally, a person having a greater risk of developing a neoplasm (e.g., one who is genetically predisposed or one who previously had a neoplasm) may receive prophylactic treatment to inhibit or delay neoplastic formation.

The dosage and frequency of administration of each component of the combination can be controlled independently. For example, one compound may be administered orally three times per day, while the second compound may be administered intramuscularly once per day. The compounds may also be formulated together such that one administration delivers both compounds. Formulations and dosages are described further below.

Formulation of Pharmaceutical Compositions

The administration of each compound of the combination may be by any suitable means that results in a concentration of the compound that, combined with the other component, is anti-neoplastic upon reaching the target region. The compound may be contained in any appropriate amount in any suitable carrier substance, and is generally present in an amount of 1–95% by weight of the total weight of the composition. The composition may be provided in a dosage form that is suitable for the oral, parenteral (e.g., intravenously, intramuscularly), rectal, cutaneous, nasal, vaginal, inhalent, skin (patch), or ocular administration route. Thus, the composition may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, or aerosols. The pharmaceutical compositions may be formulated according to conventional pharmaceutical practice (see, e.g., *Remington: The Science and Practice of Pharmacy,* (19th ed.) ed. A. R. Gennaro, 1995, Mack Publishing Company, Easton, Pa. and *Encyclopedia of Pharmaceutical Technology,* eds. J. Swarbrick and J. C. Boylan, 1988–1999, Marcel Dekker, New York.

Pharmaceutical compositions according to the invention may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance (sawtooth kinetic pattern); (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of compounds in the form of a controlled release formulation is especially preferred in cases in which the compound, either alone or in combination, has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose ($LD_{50}$) to median effective dose ($ED_{50}$)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes.

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in *Encyclopedia of Pharmaceutical Technology,* supra.

The two drugs may be mixed together in the tablet, or may be partitioned. In one example, the first drug is contained on the inside of the tablet, and the second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled Release Oral Dosage Forms

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated metylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the compounds of the claimed combinations may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the drug(s) with excipients and 20–75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable dispersing or wetting agents are, for example, naturally-occurring phosphatides (e.g., lecithin or condensation products of ethylene oxide with a fatty acid, a long chain aliphatic alcohol, or a partial ester derived from fatty acids) and a hexitol or a hexitol anhydride (e.g., polyoxyethylene stearate, polyoxyethylene sorbitol monooleate, polyoxyethylene sorbitan monooleate, and the like). Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions is well-known to those skilled in the art of pharmaceutical formulation. Formulations can be found in *Remington: The Science and Practice of Pharmacy*, supra.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. Furthermore, the composition may include suspending, solubilizing, stabilizing, pH-adjusting agents, and/or dispersing agents.

As indicated above, the pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10–60% w/w of propylene glycol or the like.

Controlled Release Parenteral Compositions

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices.

Materials for use in the preparation of microspheres and/or microcapsules are, e.g., biodegradable/bioerodible polymers such as polyglactin, poly-(isobutyl cyanoacrylate), poly(2-hydroxyethyl-L-glutamnine) and, poly(lactic acid). Biocompatible carriers that may be used when formulating a controlled release parenteral formulation are carbohydrates (e.g., dextrans), proteins (e.g., albumin), lipoproteins, or antibodies.

Materials for use in implants can be non-biodegradable (e.g., polydimethyl siloxane) or biodegradable (e.g., poly (caprolactone), poly(lactic acid), poly(glycolic acid) or poly (ortho esters)).

Rectal Compositions

For rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols and polyoxyethylene sorbitan fatty acid esters. Various additives, enhancers, or surfactants may be incorporated.

Compositions for Inhalation

For administration by inhalation, typical dosage forms include nasal sprays and aerosols. In a typically nasal formulation, the active ingredient(s) are dissolved or dispersed in a suitable vehicle. The pharmaceutically acceptable vehicles and excipients (as well as other pharmaceutically acceptable materials present in the composition such as diluents, enhancers, flavoring agents, and preservatives) are selected in accordance with conventional pharmaceutical practice in a manner understood by the persons skilled in the art of formulating pharmaceuticals.

Percutaneous and Topical Compositions

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gelforming agents, ointment bases, perfumes, and skin protective agents.

Examples of emulsifying agents are naturally occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof tetrahydrofurfuryl alcohol, and AZONE™. Examples of chelating agents are sodium EDTA, citric acid, and phosphoric acid. Examples of gel forming agents are CARBOPOL™, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (TWEEN™)).

The pharmaceutical compositions described above for topical administration on the skin may also be used in connection with topical administration onto or close to the part of the body that is to be treated. The compositions may be adapted for direct application or for introduction into relevant orifice(s) of the body (e.g., rectal, urethral, vaginal or oral orifices). The composition may be applied by means of special drug delivery devices such as dressings or alternatively plasters, pads, sponges, strips, or other forms of suitable flexible material.

Controlled Release Percutaneous and Topical Compositions

There are several approaches for providing rate control over the release and transdermal permeation of a drug, including: membrane-moderated systems, adhesive diffusion-controlled systems, matrix dispersion-type systems, and microreservoir systems. A controlled release percutaneous and/or topical composition may be obtained by using a suitable mixture of the above-mentioned approaches.

In a membrane-moderated system, the active drug is present in a reservoir which is totally encapsulated in a shallow compartment molded from a drug-impermeable laminate, such as a metallic plastic laminate, and a rate-controlling polymeric membrane such as a microporous or a non-porous polymeric membrane (e.g., ethylene-vinyl acetate copolymer). The active compound is only released through the rate-controlling polymeric membrane. In the drug reservoir, the active drug substance may either be dispersed in a solid polymer matrix or suspended in a viscous liquid medium such as silicone fluid. On the external surface of the polymeric membrane, a thin layer of an adhesive polymer is applied to achieve an intimate contact of the transdermal system with the skin surface. The adhesive polymer is preferably a hypoallergenic polymer that is compatible with the active drug.

In an adhesive diffusion-controlled system, a reservoir of the active drug is formed by directly dispersing the active drug in an adhesive polymer and then spreading the adhesive containing the active drug onto a flat sheet of substantially drug-impermeable metallic plastic backing to form a thin drug reservoir layer. A matrix dispersion-type system is characterized in that a reservoir of the active drug substance is formed by substantially homogeneously dispersing the active drug substance in a hydrophilic or lipophilic polymer matrix and then molding the drug-containing polymer into a disc with a substantially well-defined surface area and thickness. The adhesive polymer is spread along the circumference to form a strip of adhesive around the disc.

In a microreservoir system, the reservoir of the active substance is formed by first suspending the drug solids in an aqueous solution of water-soluble polymer, and then dispersing the drug suspension in a lipophilic polymer to form a plurality of microscopic spheres of drug reservoirs.

Dosages

The dosage of each compound of the claimed combinations depends on several factors, including: the administration method, the disease to be treated, the severity of the disease, whether the disease is to be treated or prevented, and the age, weight, and health of the person to be treated.

The compounds are preferably administered in an amount of about 0.1–30 mg/kg body weight per day, and more preferably in an amount of about 0.5–15 mg/kg body weight per day. As described above, the compound in question may be administered orally in the form of tablets, capsules, elixirs or syrups, or rectally in the form of suppositories. Parenteral administration of a compound is suitably performed, for example, in the form of saline solutions or with the compound incorporated into liposomes. In cases where the compound in itself is not sufficiently soluble to be dissolved, a solubilizer such as ethanol can be applied. Below, for illustrative purposes, the dosages for benzimidazoles and pentamidine are described. One in the art will recognize that if a second compound is substituted for either a benzimidazole or pentamidine, the correct dosage can be determined by examining the efficacy of the compound in cell proliferation assays, as well as its toxicity in humans.

Oral Administration

For a benzimidazole adapted for oral administration for systemic use, the dosage is normally about 1 mg to 1000 mg per dose administered (preferably about 5 mg to 500 mg, and more preferably about 10 mg to 300 mg) one to ten times daily (preferably one to five times daily) for one day to one year, and may even be for the life of the patient; because the combinations of the invention function primarily as cytostatic rather than cytotoxic agents, and exhibit low toxicity, chronic, long-term administration will be indicated in many cases. Dosages up to 8 g per day may be necessary.

For pentamidine, the dosage is normally about 0.1 mg to 300 mg per dose administered (preferably about 1 mg to 100 mg) one to four times daily for one day to one year, and, like a benzimidazole, may be administered for the life of the patient. Administration may also be given in cycles, such that there are periods during which time pentamidine is not administered. This period could be, for example, about a day, a week, a month, or a year or more.

Rectal Administration

For compositions adapted for rectal use for preventing disease, a somewhat higher amount of a compound is usually preferred. Thus a dosage of a benzimidazole is normally about 5 mg to 2000 mg per dose (preferably about 10 mg to 1000 mg, more preferably about 25 mg to 500 mg) administered one to four times daily. Treatment durations are as described for oral admininstration. The dosage of pentamidine is as described for orally admininstered pentamidine.

Parenteral Administration

For intravenous or intramuscular administration of a benzimidazole, a dose of about 0.1 mg/kg to about 100 mg/kg body weight per day is recommended, a dose of about 1 mg/kg to about 25 mg/kg is preferred, and a dose of 1 mg/kg to 10 mg/kg is most preferred. Pentamidine is administered at a dose of about 0.1 mg/kg to about 20 mg/kg, preferably at a dose of about 0.5 mg/kg to about 10 mg/kg, and more preferably at a dose of about 1 mg/kg to about 4 mg/kg.

Each compound is usually administered daily for up to about 6 to 12 months or more. It may be desirable to administer a compound over a one to three hour period; this period may be extended to last 24 hours or more. As is described for oral administration, there may be periods of about one day to one year or longer during which at least one of the drugs is not administered.

Inhalation

For inhalation, a benzimidazole is administered at a dose of about 1 mg to 1000 mg daily, and preferably at a dose of about 10 mg to 500 mg daily. For pentamidine, a dose of about 10 mg to 1000 mg, and preferably at a dose of 30 mg to 600 mg, is administered daily.

Percutaneous Administration

For topical administration of either compound, a dose of about 1 mg to about 5 g administered one to ten times daily for one week to 12 months is usually preferable.

The following examples are to illustrate the invention. They are not meant to limit the invention in any way.

EXAMPLE 1

Preparation of the Albendazole/Pentamidine Isethionate Dilution Matrix

Stock solutions of albendazole and pentamidine isethionate (Sigma catalog number A4673 and P0547, respectively) were made in dimethylsulfoxide (DMSO) at concentrations of 15.07 mM and 6.74 mM respectively. An 8× stock solution (128 $\mu$M) of each individual compound was made in Dulbecco's Modified Eagle Medium (DMEM) (Gibco 11995-040) containing 10% fetal bovine serum (FBS), 200 mM L-glutamine, and 1% antibiotic/antimycotic solution. From this a 2-fold dilution series was made in DMEM. This series provided nine concentrations ranging from 64 $\mu$M to 240 nM, and one concentration of 0 M. The compound mixture matrix was prepared by filling columns of a 384-well plate with the dilution series of pentamidine isethionate (first column: 32 $\mu$M; second column: 16 $\mu$M; third column: 8 $\mu$M; fourth column: 4 $\mu$M; fifth column: 2 $\mu$M; sixth column: 1 $\mu$M; seventh column: 500 nM; eighth column: 250 nM; ninth column: 125 nM; and tenth column: no compound) and filling the rows with the dilution series of albendazole (first row: 32 $\mu$M; second row: 16 $\mu$M; third row: 8 $\mu$M; fourth row: 4 $\mu$M; fifth row: 2 $\mu$M; sixth row: 1 $\mu$M; seventh row: 500 nM; eighth row: 250 nM; ninth row: 125 nM; and tenth row: no compound) using a 16-channel pipettor (Finnpipette). This compound mixture plate provided 4× concentrations of each compound that are transferred to assay plates. The dilution matrix thus contained 100 different points—81 wells where varying amounts of a benzimidazole and pentamidine were present, as well as a ten-point dilution series (2-fold) for each individual compound.

EXAMPLE 2

Assay for Antiproliferative Activity of Albendazole and Pentamidine Isethionate

The compound dilution matrix was assayed using the A549 bromodeoxyuridine (BrdU) cytoblot method. Forty-five microliters of a suspension containing A549 lung adenocarcinoma cells (ATCC# CCL-1 85) was seeded in a white opaque polystyrene cell culture treated sterile 384-well plate (NalgeNunc #164610) using a multidrop (Labsystems) to give a density of 3000 cells per well. Fifteen microliters of the 4× compound mixture matrix was added to each well of the plate containing the cells. The compound mixture matrix was transferred using a 16-channel pipettor (Finnpipette). In addition, control wells with paclitaxel (final concentration 4.6 $\mu$M), podophyllotoxin (9.6 $\mu$M), and quinacrine (8.5 $\mu$M) were added to each plate. Each experiment was conducted in triplicate plates.

After incubation for 48 hours at 37° C., BrdU was added to each well at a concentration of 10 $\mu$M. After 16 hours, the media was aspirated and the cells were fixed by the addition of 70% ethanol and phosphate-buffered saline (PBS) at room temperature for 1 hour. The fixative was aspirated and 2N HCl with Tween 20 (polyoxyethylene sorbitan monolaurate) was added to each well and the plates were incubated for 20 minutes at room temperature. The HCl was neutralized with a solution of 2N NaOH and the cells were washed twice with Hank's Balanced Salt Solution (HBSS) and once with PBS containing 0.5% bovine serum albumin (BSA) and 0.1% Tween 20. The wash solution was removed and mouse anti-BrdU primary antibody (PharMingen #555627) was diluted 1:1000 in PBS containing BSA, Tween 20, and secondary antibody at a dilution of 1:2000 (Amersham #NA931). The secondary antibody recognizes the mouse antibody and is conjugated to the enzyme horseradish peroxidase (HRP). After one hour of incubation, the antibody solution was removed and the cells washed once with PBS. After the PBS wash, the HRP substrate (which contains luminol, hydrogen peroxide, and an enhancer such as para-iodophenol) was added to each well. The plates were read using an LJL Analyst. All aspirations as well as the washes with PBS and HBSS were performed using a TECAN™ Power Washer 384. The amount of light output from each well indicates the amount of DNA synthesis that occurred in that well. Decreased light indicates antiproliferative action of the compounds.

Luminescence for each position in the albendazole/pentamidine isethionate dilution matrix was divided into the luminescence values for A549 cells treated with only DMSO vehicle, providing antiproliferative ratios for each position in the albendazole/pentamidine isethionate dilution matrix. Antiproliferative ratios were also calculated for paclitaxel, podophyllotoxin, and quinacrine and used for comparison.

TABLE 1

| Albendazole Concentrations | Pentamidine Isethionate Concentrations ($\mu$M) | | | | | | | | | |
|---|---|---|---|---|---|---|---|---|---|---|
| ($\mu$M) | 8 | 4 | 2 | 1 | 0.5 | 0.25 | 0.13 | 0.06 | 0.03 | 0 |
| 8 | 7.4 | 8.0 | 5.7 | 5.2 | 6.2 | 6.5 | 4.5 | 4.1 | 4.3 | 3.1 |
| 4 | 9.9 | 9.5 | 9.4 | 8.9 | 6.8 | 4.9 | 3.7 | 3.0 | 2.4 | 2.4 |
| 2 | 8.7 | 5.8 | 7.0 | 5.1 | 4.3 | 4.0 | 3.2 | 2.8 | 3.1 | 2.5 |
| 1 | 6.6 | 5.7 | 5.5 | 4.6 | 3.4 | 3.1 | 2.9 | 2.1 | 1.9 | 1.4 |
| 0.5 | 6.9 | 5.9 | 4.8 | 3.9 | 2.3 | 1.7 | 1.9 | 1.5 | 1.3 | 1.2 |
| 0.25 | 5.5 | 5.5 | 4.9 | 3.1 | 1.9 | 1.5 | 1.4 | 1.4 | 1.2 | 1.3 |
| 0.13 | 4.5 | 4.2 | 3.0 | 1.8 | 1.4 | 1.2 | 1.2 | 1.2 | 1.1 | 1.2 |
| 0.06 | 3.3 | 3.2 | 2.2 | 1.5 | 1.1 | 1.0 | 1.1 | 1.0 | 1.1 | 0.9 |
| 0.03 | 4.0 | 3.2 | 2.0 | 1.4 | 1.3 | 1.4 | 1.2 | 1.2 | 1.0 | 1.3 |
| 0 | 2.5 | 2.2 | 1.9 | 1.3 | 1.1 | 1.2 | 0.9 | 1.0 | 1.0 | 0.9 |

At 2.0 $\mu$M, pentamidine isethionate alone yields an antiproliferative ratio of 1.9 (i.e., inhibition of 47% of growth) and this increases to a ratio of 2.2 (inhibition of 55% of growth) when the concentration is doubled to 4.0 $\mu$M. Two micromolar albendazole yields a ratio of 2.5 (inhibition of 60% of growth), and this is increased no further by doubling the concentration to 4.0 μM. When 2.0 μM pentamidine isethionate is tested in combination with 2.0 μM albendazole (4.0 μM total compound species), an antiproliferative ratio of 7.0 is achieved (inhibition of 85.7% of growth). Thus, a combination of albendazole and pentamidine isethionate yields an antiproliferative ratio higher than that seen for paclitaxel (4.0), an effect that was not achieved by either drug alone.

The combination of thiabendazole and pentamidine isethionate did not result in greater antiproliferative activity than either drug alone (Table 4). These results are consistent with the findings by Gupta (*Mol. Pharmacol.* 30:142–148, 1986) of a lack of cross-resistance of the nocodozole-resistant NocR and Podrii6 cell lines to thiabendazole (but not to other benzimidazoles tested), indicating that the mechanism of action of this compound is different from that of other benzimidazoles.

TABLE 2

| Mebendazole Concentrations (μM) | Pentamidine Isethionate Concentrations (μM) | | | | | | | | | |
|---|---|---|---|---|---|---|---|---|---|---|
| | 4 | 2 | 1 | 0.5 | 0.25 | 0.13 | 0.06 | 0.03 | 0.015 | 0 |
| 4 | 12.2 | 9.8 | 6.2 | 4.5 | 5.1 | 4.6 | 4.9 | 5.0 | 4.5 | 4.4 |
| 2 | 14.3 | 12.2 | 6.7 | 5.5 | 4.7 | 5.4 | 5.0 | 6.0 | 5.1 | 5.0 |
| 1 | 8.9 | 10.9 | 7.8 | 4.1 | 3.7 | 3.6 | 3.7 | 3.9 | 3.9 | 3.4 |
| 0.5 | 10.2 | 11.5 | 6.5 | 4.7 | 3.3 | 3.4 | 3.0 | 3.1 | 3.0 | 2.8 |
| 0.25 | 6.6 | 5.9 | 3.8 | 1.7 | 1.5 | 1.5 | 1.4 | 1.5 | 1.6 | 1.5 |
| 0.13 | 5.7 | 4.6 | 2.4 | 1.5 | 1.3 | 1.3 | 1.2 | 1.4 | 1.4 | 1.5 |
| 0.06 | 4.5 | 3.4 | 1.9 | 1.1 | 1.0 | 1.0 | 1.1 | 0.9 | 1.2 | 1.0 |
| 0.03 | 5.4 | 5.1 | 2.3 | 1.5 | 1.4 | 1.3 | 1.3 | 1.4 | 1.3 | 1.4 |
| 0.015 | 5.1 | 3.2 | 1.9 | 1.1 | 1.1 | 1.0 | 1.0 | 0.9 | 1.2 | 1.0 |
| 0 | 5.7 | 4.1 | 2.4 | 1.5 | 1.2 | 1.4 | 1.2 | 1.4 | 1.6 | 1.7 |

TABLE 3

| Oxibendazole Concentrations (μM) | Pentamidine Isethionate Concentrations (μM) | | | | | | | | | |
|---|---|---|---|---|---|---|---|---|---|---|
| | 4 | 2 | 1 | 0.5 | 0.25 | 0.13 | 0.06 | 0.03 | 0.015 | 0 |
| 4 | 6.7 | 6.6 | 4.6 | 3.7 | 3.9 | 3.6 | 3.7 | 3.8 | 3.7 | 3.6 |
| 2 | 6.3 | 6.6 | 4.9 | 3.5 | 3.0 | 2.8 | 2.5 | 3.5 | 2.9 | 3.2 |
| 1 | 5.2 | 6.4 | 4.8 | 3.2 | 3.1 | 2.7 | 3.0 | 3.1 | 3.3 | 2.9 |
| 0.5 | 5.0 | 5.8 | 3.9 | 2.7 | 2.6 | 2.8 | 1.5 | 1.7 | 1.7 | 1.6 |
| 0.25 | 5.0 | 4.1 | 3.5 | 1.5 | 1.2 | 1.2 | 1.1 | 1.0 | 1.2 | 1.0 |
| 0.13 | 4.0 | 3.8 | 2.1 | 1.2 | 1.1 | 1.1 | 1.1 | 1.1 | 1.0 | 1.1 |
| 0.06 | 3.6 | 3.0 | 1.8 | 1.0 | 1.0 | 1.1 | 1.1 | 1.0 | 1.3 | 1.0 |
| 0.03 | 3.5 | 3.0 | 1.7 | 1.2 | 1.0 | 1.1 | 1.0 | 1.2 | 0.9 | 1.1 |
| 0.015 | 3.9 | 2.8 | 1.9 | 1.1 | 1.0 | 1.0 | 1.0 | 0.9 | 1.0 | 1.0 |
| 0 | 4.1 | 2.9 | 1.6 | 1.3 | 0.9 | 1.1 | 1.1 | 1.0 | 1.1 | 1.2 |

In another analysis, the potency of the single compounds is shifted by the presence of the other compound. The maximal antiproliferative ratio achieved by albendazole alone was 3.1 (at 8.0 μM). A similar antiproliferative ratio was observed when 1 μM pentamidine isethionate was combined with albendazole at concentrations as low as 250 nM, significantly reducing the total drug species needed to achieve this effect.

EXAMPLE 3

Assay for Antiproliferative Activity of Pentamidine Isethionate in Combination with Albendazole Sulfoxide, Mebendazole, Oxibendazole, or Thiabendazole Because albendazole shares antihelmentic activity with other benzimidazoles, we tested the combination of pentamidine isethionate with benzimidazoles mebendazole, oxibendazole, albendazole sulfoxide, and thiabendazole (Tables 2–5). The assays were performed as described in Example 2, above. In the case of mebendazole and oxibendazole, the combination of the benzimidazole with pentamidine resulted in greater antiproliferative activity than that that achieved by either drug alone (Tables 2 and 3).

TABLE 4

| Thiabendazole Concentrations (μM) | Pentamidine Isethionate Concentrations (μM) | | | | | |
|---|---|---|---|---|---|---|
| | 4 | 2 | 1 | 0.5 | 0.25 | 0 |
| 4 | 4.1 | 2.4 | 1.5 | 1.2 | 1.2 | 1.2 |
| 2 | 4.5 | 3.0 | 1.4 | 1.1 | 1.1 | 1.2 |
| 1 | 4.1 | 2.9 | 1.8 | 1.0 | 1.2 | 1.2 |
| 0.5 | 3.3 | 3.1 | 1.6 | 1.0 | 1.3 | 1.2 |
| 0.25 | 3.5 | 3.4 | 1.4 | 1.1 | 1.1 | 1.2 |
| 0 | 3.7 | 3.0 | 1.7 | 1.1 | 1.1 | 1.2 |

TABLE 5

| Albendazole Sulfoxide Concentrations (μM) | Pentamidine Isethionate Concentrations (μM) | | | | | |
|---|---|---|---|---|---|---|
| | 4 | 2 | 1 | 0.5 | 0.25 | 0 |
| 8 | 3.7 | 3.2 | 2.5 | 1.2 | 1.1 | 1.4 |
| 4 | 2.7 | 2.7 | 1.6 | 1.3 | 1.2 | 1.4 |
| 2 | 2.5 | 1.9 | 1.7 | 1.1 | 1.1 | 1.2 |
| 1 | 1.8 | 2.4 | 1.4 | 1.0 | 1.0 | 1.1 |
| 0.5 | 1.8 | 1.8 | 1.6 | 1.1 | 0.9 | 1.2 |
| 0 | 1.9 | 2.1 | 1.6 | 0.9 | 1.1 | 1.0 |

The anti-proliferative effect demonstrated with A459 cells can be similarly demonstrated using other cancer cell lines, such as MCF7 mammary adenocarcinoma, PA-1 ovarian teratocarcinoma, HT29 colorectal adenocarcinoma, H1299 large cell carcinoma, U-2 OS osteogenic sarcoma, U-373 MG glioblastoma, Hep-3B hepatocellular carcinoma, BT-549 mammary carcinoma, T-24 bladder cancer, C-33A cervical carcinoma, HT-3 metastatic cervical carcinoma, SiHa squamous cervical carcinoma, CaSki epidermoid cervical carcinoma, NCI-H292 mucoepidermoid lung carcinoma, $NC_{1-2030}$ non small cell lung carcinoma, HeLa, epithelial cervical adenocarcinoma, KB epithelial mouth carcinoma, HT1080 epithelial fibrosarcoma, Saos-2 epithelial osteogenic sarcoma, PC3 epithelial prostate adenocarcinoma, SW480 colorectal carcinoma, CCL-228, and MS-751 epidermoid cervical carcinoma cell lines. Specificity can be tested by using cells such as NHLF lung fibroblasts, NHDF dermal fibroblasts, HMEC mammary epithelial cells, PrEC prostate epithelial cells, HRE renal epithelial cells, NHBE bronchial epithelial cells, CoSmC Colon smooth muscle cells, CoEC colon endothelial cells, NHEK epidermal keratinocytes, and bone marrow cells as control cells.

Other Embodiments

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology or related fields are intended to be within the scope of the invention.

What is claimed is:

1. A pharmaceutical composition comprising a pharmaceutically acceptable carrier and the drugs (i) pentamidine or a salt thereof, and (ii) albendazole, albendazole sulfonate, albendazole sulfone, or albendazole sulfoxide; wherein drugs (i) and (ii) are each present in a synergistically effective amount that, when administered together to a patient having a cancer selected from the group consisting of brain cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, or uterine cancer, inhibits the growth of said cancer.

2. The composition of claim 1, wherein drug (ii) is present in said composition in an amount of 10 to 2500 milligrams and drug (i) is present in said composition in an amount of 1 to 1000 milligrams.

3. The method of claim 2, wherein drug (ii) is present in said composition in an amount of 50 to 1000 milligrams and drug (i) is present in said composition in an amount of 10 to 250 milligrams.

4. The composition of claim 1, wherein said composition is formulated for intravenous, intramuscular, rectal, inhalation, or oral administration.

5. The composition of claim 1, wherein said drug (i) is pentamidine isethionate.

6. The composition of claim 1, wherein said drug (i) is pentamidine isethionate and said drug (ii) is albendazole.

7. The composition of claim 1, wherein said drug (i) is pentamidine isethionate and said drug (ii) is albendazole sulfonate.

8. The composition of claim 1, wherein said drug (i) is pentamidine isethionate and said drug (ii) is albendazole sulfone.

9. The composition of claim 1, wherein said drug (i) is pentamidine isethionate and said drug (ii) is albendazole sulfoxide.

10. A method for treating a patient having a cancer selected from the group consisting of brain cancer, breast cancer, cervical cancer, colon cancer, gastric cancer, kidney cancer, leukemia, liver cancer, lymphoma, ovarian cancer, pancreatic cancer, prostate cancer, rectal cancer, sarcoma, skin cancer, testicular cancer, or uterine cancer, said method comprising administering to said patient the drugs (i) pentatnidine or a salt thereof, and (ii) albendazole, albendazole salfonate, albendazole sulfone, or albendazole sulfoxide, wherein the drugs (i) and (ii) are administered simultaneously or within 14 days of each other, in amounts sufficient to inhibit the growth of said cancer in said patient.

11. The method of claim 10, wherein drugs (i) and (ii) are administered within ten days of each other.

12. The method of claim 11, wherein drugs (i) and (ii) are administered within five days of each other.

13. The method of claim 12, wherein drugs (i) and (ii) are administered within twenty-four hours of each other.

14. The method of claim 13, wherein said cancer is lung cancer.

15. The method of claim 14, wherein said lung cancer is selected from the group consisting of squamous cell carcinoma, adenocarcinoma, and large cell carcinoma.

16. The method of claim 13, wherein said cancer is selected from the group consisting of colon cancer, breast cancer, and prostate cancer.

17. The method of claim 13, wherein said drug (i) is pentamidine isethionate and said drug (ii) is albendazole.

18. The method of claim 13, wherein said drug (i) is pentamidine isethionate and said drug (ii) is albendazole sulfonate.

19. The method of claim 13, wherein said drug (i) is pentamidine isethionate and said drug (ii) is albendazole sulfone.

20. The method of claim 13, wherein said drug (i) is pentamidine isethionate and said drug (ii) is albendazole sulfoxide.

21. The method of claim 1, wherein said cancer is lung cancer.

22. The method of claim 21, wherein said lung cancer is selected from the group consisting of squamous cell carcinoma, adeno carcinoma, and large cell carcinoma.

23. The method of claim 10, wherein drugs (i) and (ii) are administered to said patient by intravenous, intramuscular, inhalation, rectal, or oral administration.

24. The method of claim 1, wherein said drug (i) is pentamidine isethionate, pentamidine platinum, pentamidine dihydrochioride or pentamidine dimethanesulfonate.

25. The method of claim 10, wherein said drug (i) is pentamidine isethionate and said drug (ii) is albendazole.

26. The method of claim 10, wherein said drug (i) is pentamidine isethionate and said drug (ii) is albendazole sulfonate.

27. The method of claim 10, wherein said drug (i) is pentamidine isethionate and said drug (ii) is albendazole sulfone.

28. The method of claim 10, wherein said drug (i) is pentamidine isethionate and said drug (ii) is albendazole sulfoxide.

29. The method of claim 10, wherein said cancer is selected from the group consisting of colon cancer, breast cancer, and prostate cancer.

30. A method for treating a patient having a cancer selected from the group consisting of brain cancer, breast cancer, cervical cancer, colon cancer, gastric cancer, kidney cancer, leukemia, liver cancer, lymnphoma, ovarian cancer, pancreatic cancer, prostate cancer, rectal cancer, sarcoma, skin cancer, testicular cancer, or uterine cancer, said method comprising administering to said patient a pharmaceutical composition comprising a pharmaceutically acceptable carrier and the drugs (i) pentamidine or a salt thereof, and (ii) albendazole, albendazole sulfonate, albendazole sulfone, or albendazole sulfoxide, at dosages that together inhibit the growth of said cancer in said patient.

31. The method of claim 30, wherein drug (ii) is present in said composition in an amount of 10 to 2500 milligrams and drug (i) is present in said composition in an amount of 1 to 1000 milligrams.

32. The method of claim 31, wherein drug (ii) is present in said composition in an amount of 50 to 1000 milligrams and drug (i) is present in said composition in an amount of 10 to 250 milligrams.

33. The method of claim 30, wherein said composition is administered to said patient by intravenous, intramuscular, inhalation, rectal, or oral administration.

34. The method of claim 30, wherein said drug (i) is pentamidine isethionate.

35. The method of claim 30, wherein said drug (i) is pentamidine isethionate and said drug (ii) is albendazole.

36. The method of claim 30, wherein said drug (i) is pentamidine isethionate and said drug (ii) is albendazole sulfonate.

37. The method of claim 30, wherein said drug (i) is pentamidine isethionate and said drug (ii) is albendazole sulfone.

38. The method of claim 30, wherein said drug (i) is pentamidine isethionate and said drug (ii) is albendazole sulfoxide.

39. The method of claim 30, wherein said cancer is lung cancer.

40. The method of claim 39, wherein said lung cancer is selected from the group consisting of squamous cell carcinoma, adenocarcinoma, and large cell carcinoma.

41. The method of claim 30, wherein said cancer is selected from the group consisting of colon cancer, breast cancer, and prostate cancer.

42. A method of treating a patient having lung cancer, said method comprising administering to said patient the drugs pentamidine isethionate and albendazole, wherein said pentamidine isethionate and albendazole are administered within twenty-four hours of each other, in amounts sufficient to inhibit the growth of said lung cancer in said patient.

43. The method of claim 42, wherein said pentamidine isethionate and albendazole are administered simultaneously.

* * * * *